United States Patent [19]

Haimowitz et al.

[11] 4,169,143

[45] Sep. 25, 1979

[54] METHOD FOR TREATING HEMORRHOID SYMPTOMS AND COMPOSITION FOR USE THEREIN

[76] Inventors: Irving Haimowitz, 15604 Harvest Ave., Norwalk, Calif. 90650; Ethel Arrington, 9759 Sharp Ave., Pacoima, Calif. 91331

[21] Appl. No.: 923,142

[22] Filed: Jul. 10, 1978

[51] Int. Cl.$^2$ .................. A61K 35/78; A61K 31/355; A61K 31/12
[52] U.S. Cl. .................................... 424/195; 424/284; 424/331
[58] Field of Search ............................... 424/195, 284

[56] References Cited

U.S. PATENT DOCUMENTS

| 444,411 | 1/1891 | Trent | 424/331 |
|---|---|---|---|
| 2,582,395 | 1/1952 | Rigby | 424/284 |

OTHER PUBLICATIONS

Remington's Pharm. Sci. 15th Ed., 1975, Mack Publishing Co., Easton, Pa., pp. 715, 1249, 1523, 1524, 1529 & 1531.
1st Documentary Edition of American Perfumes & Aromatics, pp. 76 & 78—PTO library, Feb. 17, 1960.
FDA Consumer, Jul.—Aug. 1973, p. 24.

*Primary Examiner*—Donald B. Moyer
*Attorney, Agent, or Firm*—Robert S. Frieman

[57] ABSTRACT

A composition for use in the treatment of hemorrhoids comprising Vitamin E and a benzoin solution in a pharmacologically acceptable carrier.

10 Claims, No Drawings

METHOD FOR TREATING HEMORRHOID SYMPTOMS AND COMPOSITION FOR USE THEREIN

BACKGROUND OF THE INVENTION

1. Field of the Invention

The instant invention pertains to a method for treating hemorrhoids as well as to a composition for use therein.

2. Background of the Invention

There exists on the market several over-the-counter and prescription compositions which are alleged to give temporary relief from hemorrhoidal itch and irritation. A few of these preparations are also alleged to help shrink the swelling of hemorrhoidal tissue.

However, as many hemorrhoid sufferers are painfully aware, these preparations are at best marginally effective.

Summary of the Invention

This invention encompasses a composition which, when used in a periodic manner readily produces a remarkable shrinkage in hemorrhoidal tissue. In addition, the composition of the instant invention also is highly effective in relieving the itch, pain, and swelling due to hemorrhoidal irritation.

The composition of the instant invention comprises Vitamin E and a benzoin solution in a pharmacologically acceptable carrier.

DESCRIPTION OF THE PREFERRED EMBODIMENTS

The composition of the instant invention comprises Vitamin E and a benzoin solution in a pharmacalogically acceptable carrier.

The Vitamin E employed in the composition of the instant invention can be either natural or synthetic. Preferably, natural Vitamin E is employed in the composition of this invention.

The benzoin solution comprises gum (or resin) benzoin dissolved in a suitable solvent such as alcohol. The concentration of the benzoin solution is not critical but is preferably such that the benzoin solution readily lends itself to handling during the manufacturing process as well as during the use of the final product.

The benzoin solution preferably comprises from about 5 to 50 weight % benzoin and from about 50 to about 95 weight % of a suitable solvent. More preferably, the benzoin solution comprises from about 15 to about 25 weight % benzoin and from about 75 to about 85 weight % of a suitable solvent.

Alcohol is the preferred solvent.

A commercially available form of benzoin solution capable of use in the instant invention is benzoin tincture compound which comprises 20 weight % benzoin and 80 weight % alcohol.

Any pharmacalogically acceptable carrier known to those skilled in the art which is compatible with the other above identified constituents can be employed in the composition of this invention. Preferably, the carrier is a fat soluble carrier. More preferably, the fat soluble carrier is lanolin. Anhydrous lanolin is the carrier of choice.

The exact formulation of the composition of the instant invention is not critical. Preferably, the composition of the instant invention comprises at least about 200, more preferably from about 300 to about 1,000 and 400 to about 800, and optimally about 500 International Units (IU) of Vitamin E per gram of carrier.

With respect to benzoin, it is preferred that the composition of the instant invention comprise at least about 0.02, more preferably from about 0.025 to about 0.07 and from about 0.03 to about 0.05, and optimally about 0.035 grams of benzoin per gram of carrier.

When the benzoin is present in a benzoin solution comprising 20 weight % benzoin and 80 weight % alcohol, it is preferred that the composition of the instant invention comprise at least about 0.01, more preferably about 0.125 to about 0.35 and from about 0.15 to about 0.25, and optimally about 0.175 grams of said solution per gram of carrier.

The composition of the instant invention can be employed by any topically suitable means to external hemorrhoids. Internal hemorrhoids can be treated by introducing an effective amount of the composition to the inner side of the external sphincter in a suitable suppository form, by injecting it in a reuseable or disposable syringe or by any other suitable means.

The following example is provided for the purpose of further illustration only and is not intended to be a limitation on the disclosed invention.

EXAMPLE 1

Approximately 1.5 cc of a composition comprising, per gram of anhydrous lanolin, 500 IU natural Vitamin E, 0.175 gm benzoin solution (20 weight % benzoin, 80 weight % alcohol) was periodically injected three times per day into the anus of a person with severe hemorrhoid symptoms and rectal bleeding. After three days of this treatment, the hemorrhoids evidenced a significant decrease in size and rectal bleeding completely ceased.

Based on this disclosure, many other modifications and ramifications will naturally suggest themselves to those skilled in the art. These are intended to be comprehended as within the scope of this invention.

The embodiments of the invention is which on exclusive property or privilege is claimed are defined as follows:

1. A composition comprising:
   (a) at least about 200 IU of Vitamin E; and
   (b) at least about 0.02 gm of benzoin; per gram of a pharmacologically acceptable carrier.

2. The composition of claim 1 comprising:
   (a) from about 300 to about 1,000 IU of Vitamin E; and
   (b) from about 0.025 to about 0.07 gm of benzoin; per gram of said carrier.

3. The composition of claim 2 comprising:
   (a) from about 400 to about 800 IU of Vitamin E; and
   (b) from about 0.03 to about 0.05 gm of benzoin; per gram of said carrier.

4. The composition of claim 3 comprising:
   (a) about 500 IU of Vitamin E; and
   (b) about 0.035 gm of benzoin; per gram of said carrier.

5. The composition of claim 4 wherein said Vitamin E is a natural Vitamin E and wherein said carrier is anhydrous lanolin.

6. The composition of claim 1 wherein carrier is a fat soluble carrier.

7. The composition of claim 6 wherein said fat soluble carrier is lanolin.

8. The composition of claim 7 wherein said lanolin is anhydrous lanolin and wherein said Vitamin E is natural Vitamin E.

9. The composition of claim 1 wherein said benzoin is present in a solution comprising about 20 weight % benzoin and 80 weight % alcohol.

10. A method of treating hemorrhoids comprising periodically applying thereto an effective amount of the composition of claim 1.

* * * * *